US00PP36369P2

(12) United States Plant Patent
Lim

(10) Patent No.: US PP36,369 P2
(45) Date of Patent: Jan. 7, 2025

(54) CLIMBING ROSE PLANT NAMED 'BAISIKOMIK'

(50) Latin Name: *Rosa hybrida*
Varietal Denomination: BAISIKOMIK

(71) Applicant: The Conard Pyle Company, West Grove, PA (US)

(72) Inventor: Ping Lim, Yamhill, OR (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/779,411

(22) Filed: Jul. 22, 2024

(30) Foreign Application Priority Data

Oct. 5, 2023 (QZ) ..... PBR 2023/2098

(51) Int. Cl.
*A01H 5/02* (2018.01)
*A01H 6/74* (2018.01)

(52) U.S. Cl.
USPC ..... Plt./115

(58) Field of Classification Search
USPC ..... Plt./101, 109, 115
See application file for complete search history.

(56) References Cited

U.S. PATENT DOCUMENTS

PP4,225 P 3/1978 Buck
PP18,564 P3 3/2008 Meilland

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct variety of climbing rose plant, referred to by its cultivar name, 'BAISIKOMIK', is described. The new variety forms nice turbinated shaped flowers with true color gradation. The flowers emit a strong, sweet licorice/anise fragrance. Improved reblooming is exhibited. Additionally, the new variety is particularly well suited for growing as distinctive ornamentation in the landscape.

1 Drawing Sheet

Latin name of genus and species of plant claimed: *Rosa hybrida.*

Variety denomination: 'BAISIKOMIK'.

CROSS REFERENCE TO RELATED APPLICATIONS

This application claims priority to Plant Breeders' Right Application No. 2023/2098, which was filed at Community Plant Variety Office in the European Union on Oct. 5, 2023, the contents of which are hereby incorporated by reference for all purposes.

STATEMENT REGARDING PRIOR DISCLOSURES BY THE INVENTOR

The first sale or offer for sale of the new variety was Aug. 1, 2023, in France to on the website Meilland Richardier (meillandrichardier.com). The first offer for sale of the new variety, and subsequent offer for sales and sales, was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding in St. Paul, Minnesota, United States of America by artificial pollination wherein two parents were crossed which previously had been studied in the hope that they would contribute the desired characteristics. The female parent (i.e., the seed parent) of the new variety was the 'Bucbi' variety (U.S. Plant Pat. No. 4,225). The male parent (i.e., the pollen parent) of the new variety was the 'NOATRAUM' variety (not patented).

The parentage of the new variety can be summarized as follows:

'Bucbi' x 'NOATRAUM'

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, and hardwood cuttings. Asexual propagation by the above-mentioned techniques in Le Cannet des Maures, Var, France has shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms nice turbinated shaped blossoms, (b) emits a strong, sweet licorice/anise fragrance, and (c) exhibits improved reblooming.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the 'Bucbi' variety (i.e., the seed parent) displays pink colored flowers compared to the flowers of the new variety that display petals with true color gradation in multiple shades of red and pink. Additionally, the new variety exhibits a climbing growth habit, whereas the 'NOATRUM' variety (i.e., the pollen parent) exhibits a shrub-like habit. Moreover, the new variety can be readily distinguished from non-parental related similar varieties. For example, the 'Meigrappo' variety (U.S. Plant Pat. No. 18,564) displays vermillion, red colored blossoms that lack fragrance compared to the multi-shaded red and pink colored blossoms of the new variety that emit a strong, sweet licorice fragrance.

The new variety has been named the 'BAISIKOMIK' variety.

BRIEF DESCRIPTION OF THE PHOTOGRAPHS

The accompanying photograph shows, as nearly true as it is reasonably possible to make the same in a color illustration of this character, typical specimens of the plant parts of the new variety. The rose plants of the new variety were approximately nine years of age and were observed during May while budded on their own roots and growing outdoors at Le Cannet des Maures, Var, France. Dimensions in centimeters are indicated at the bottom of the photograph.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms. The R.H.S. Colour Chart designation used herein represents the closest color observed on the majority of the specified botanical feature. The description is based on a nine-year-old specimen of the new variety, observed during May, while budded on its own roots and growing outdoors at Le Cannet des Maures, Var, France.

Botanical classification: *Rosa hybrida* cultivar 'BAISIKOMIK'.

Commercial classification: Climbing Rose Plant.

Plant:

*Habit*.—Climbing.

*Height*.—Typically between 200.0 cm to 300.0 cm.

*Width*.—Typically between 300.0 cm to 400.0 cm.

Branches:

*Stem color*.—Young stems: Yellow-Green Group 146B more or less suffused with Greyed-Purple Group 183A (the younger the wood, the more Greyed-Purple Group 183A). — adult wood: Yellow-Green Group 146B more or less suffused with Yellow-Green Group 146A.

*Length*.—From the crown to the flower is approximately 75.0 cm on average.

*Diameter*.—Approximately 1.5 cm on average.

*Thorns*.—Configuration on adult stems: concave, very elongated and curved downwards on the upper surface and very concave on the under surface. — long prickles — quantity: approximately 7 thorns on average per 10 cm long young stem and approximately 10 thorns on average per 10 cm long adult stem. — long prickles — length: typically between 0.5 cm to 1.0 cm on young stems and on adult stems. — long prickles—length at base: typically between 0.4 cm to 0.8 cm on young stems and typically between 0.5 cm and 1.0 cm on adult stems. — long prickles — width at base: typically between 0.2 cm to 0.4 cm on young stems and typically between 0.3 cm and 0.5 cm on adult stems. — long prickles — base shape: elliptical, broad and long on young stems; elliptical on adult stems. — long prickles — color on young stems: Greyed-Yellow Group 160B strongly suffused with Greyed-Purple Group 184A. — long prickles — color on adult stems: Greyed-Yellow Group 161A more or less suffused with Greyed-Red Group 180B. — small prickles — quantity: none observed.

*Internode numbers on entire branch*.—Approximately 12 on average.

*Internode length*.—Typically between 4.0 cm to 7.0 cm.

Leaflets:

*Number*.—3 and most often 5.

*Shape*.—Tip: acuminate. — base: rounded.

*Serration*.—Small and single.

*General appearance*.—Oval.

*Undulation*.—Medium.

*Glossiness of upper side*.—Weak.

*Texture*.—Moderately leathery.

*Smoothness*.—Upper surface: bumpy. — under surface: bumpy.

*Venation*.—Color is Green Group 143C suffused with Greyed-Red Group 182A when leaves are young; and pattern is imparipinnate.

*Size*.—Terminal leaflet: length is typically between 4.5 cm to 7.5 cm; width is typically between 3.0 cm to 5.0 cm. — 5-leaflet leaf. length is typically between 12.0 cm to 18.0 cm; width is typically between 10.0 cm to 15.0 cm.

Foliage:

*General appearance*.—Dense with a semi-glossy aspect.

*New foliage*.—Upper surface color: a color between Yellow-Green Group 146A and Yellow-Green Group 147A. — under surface color: a color between Yellow-Green Group 147B and Yellow-Green Group 147C.

*Adult foliage*.—Upper surface color: a color between Green Group 139A and Yellow-Green Group 147A. — under surface color: Yellow-Green Group 147B.

*Petiole*.—Texture: upper surface is glandular; under surface is prickly. — length: approximately 3.9 cm on average. — width: approximately 0.15 cm on average. — upper surface color: Yellow-Green Group 146A, strongly suffused with Greyed-Purple Group 183A when leaves are young. — under surface color: Green Group 143C.

*Rachis*.—Rachis length of terminal leaflet: approximately 5.5 cm on average. — rachis width of terminal leaflet: approximately 0.1 cm on average. — texture: upper surface is slightly glandular; under surface is prickly. — upper surface color: Yellow-Green Group 146A, strongly suffused with Greyed-Purple Group 183A when leaves are young. — under surface color: Green Group 143C.

*Stipules*.—Length: approximately 1.8 cm on average. — width: approximately 0.2 cm on average. — general appearance: rather broad. — texture: smooth. — upper surface color: Yellow-Green Group 146A. — under surface color: Yellow-Green Group 146B.

Inflorescence:

*Number of flowers per stem*.—Typically between 1 to 4 flowers per stem.

*Lastingness of the bloom*.—On the plant: approximately 15 days on average. — in vase: not tested.

*Bud*.—Shape: elongated. — size: medium — length: approximately 3.4 cm on average. — width: typically between 2.0 cm to 2.5 cm. — color as calyx breaks: upper surface: a color between Red Group 45B and Red Group 44A; basal spot is Yellow-Orange Group 14A. under surface: a color between Red Group 45C and Red Group 45D; basal spot is Yellow Group 12A.

*Sepals*.—Number: commonly 5. — length: approximately 3.0 cm on average. — width: approximately 1.0 cm on average. — shape: at the top: few elongated and narrow. at the base: flat at union with the receptacle. — extensions: typically 2 sepals with no extensions, 2 sepals with very strong extensions, and 1 sepal with medium extensions. — upper surface: texture: strongly tomentous. color: Green Group 143B evolving to Green Group 143A to the top, covered with thick hairs of White Group 155B; sepals with extensions have Greyed- Red Group 179A triangle covered with White Group 155B hairs at the base. — under surface: texture: slightly tomentous and slightly glandular. color: Green Group 143B evolving in Green Group 143A to the top.

*Receptacle*.—Color: a color in between Green Group 143A and Yellow-Green Group 144A. — length: approximately 0.9 cm on average. — width: approximately 0.9 cm on average. — surface: smooth. — shape: funnel shaped.

*Peduncle*.—Length: approximately 4.2 cm on average. — width: approximately 0.3 cm on average. — surface: little prickles. — color: a color between Yellow-Green Group 144A and Yellow-Green Group 144B.

*Flower*.—Diameter when open: typically between 8.0 cm to 9.0 cm. — depth of the flower: approximately 2.5 cm on average. — shape: cup shaped. — shape when viewed from above: irregularly rounded. — shape of the upper part of the flower profile: flat. — shape of the lower part of the flower profile: flat. — type: double. — number of petals under normal conditions: typically between 20 to 30. — petals: shape: rounded (rounded at the top and obtuse at the base). texture: thick and dry. length: typically between 2.5 cm to 3.5 cm. width: typically between 2.5 cm to 4.0 cm. — undulation of the petal: medium. — reflexing of the petal: strong. — petal incision: very weak. — petal arrangement: imbricated with few petaloids (1 to 3 per flower, appearing like half crumpled petals). — petal drop: petals drop off cleanly before drying. — fragrance: strong, sweet licorice/anise. — discoloration of the flower: none. — color when opening: basal spot on the upper surface: Yellow-Orange Group 14A. upper surface: true color gradation on the petals, starting with the basal spot of Yellow-Orange Group 14A, changing to Orange-Red Group 33B, changing to Red Group 40B, changing to Red Group 44C, and changing to Red Group 46C, in the direction from the base to the apex of the petal. basal spot on the under surface: Yellow Group 13A. under surface: true color gradation on the petals, starting with the basal spot of Yellow Group 13A, changing to Red Group 40C, and changing to Red Group 43C, in the direction from the base to the apex of the petal. — color of the open flower: basal spot on upper surface: Yellow-Orange Group 14A. upper surface: true color gradation on the petals, starting with the basal spot of Yellow-Orange Group 14A, changing to Orange-Red Group 33B, changing to Red Group 40B, and changing to Red-Purple Group 57A, in the direction from the base to the apex of the petal. The longer the flowers are open, the bigger the area of Red-Purple Group 57A on the petals becomes. basal spot on under surface: Yellow Group 13A. under surface of the flower. true color gradation on the petals, starting with the basal spot of Yellow Group 13A, changing to Red Group 40C, changing to Red Group 43C, and changing to Red-Purple Group 57D, in the direction from the base to the apex of the petal. — anthers: approximately 180 on average, length is typically 0.2 cm to 0.3 cm, width is approximately 0.1 cm on average, coloration is Yellow-Orange Group 15A, and arrangement is regular around styles. — filaments: length is typically between 0.5 cm to 0.7 cm, and coloration is Orange Group 24A. — styles: length is typically between 0.3 cm to 1.0 cm, coloration is Green-White Group 157A on basal half and Red Group 53C on upper half, and number is approximately 100 on average. — stigmas: length is typically less than 0.1 cm and coloration is Yellow-Orange Group 15C. — pollen: abundant quantity; color is Greyed-Yellow Group 162B. — hips: none observed.

Development:

*Vegetation*.—Strong.

*Blossoming*.—Very early in the season and recurrent (typically from April to October in France, with less intensity later in the season), abundant for a climbing variety.

*Resistance to diseases*.—Very good resistance for powdery mildew (*Podosphera pannosa*) and black spot (*Diplocarpon rosae*).

*Hardiness*.—Tested up to USDA Zone 5.

The new 'BAISIKOMIK' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of climbing rose plant named 'BAISIKOMIK' characterized by the following combination of characteristics:

(a) forms nice turbinated shaped blossoms, (b) emits a strong, sweet licorice/anise fragrance, and (c) exhibits improved reblooming;

substantially as herein shown and described.

* * * * *

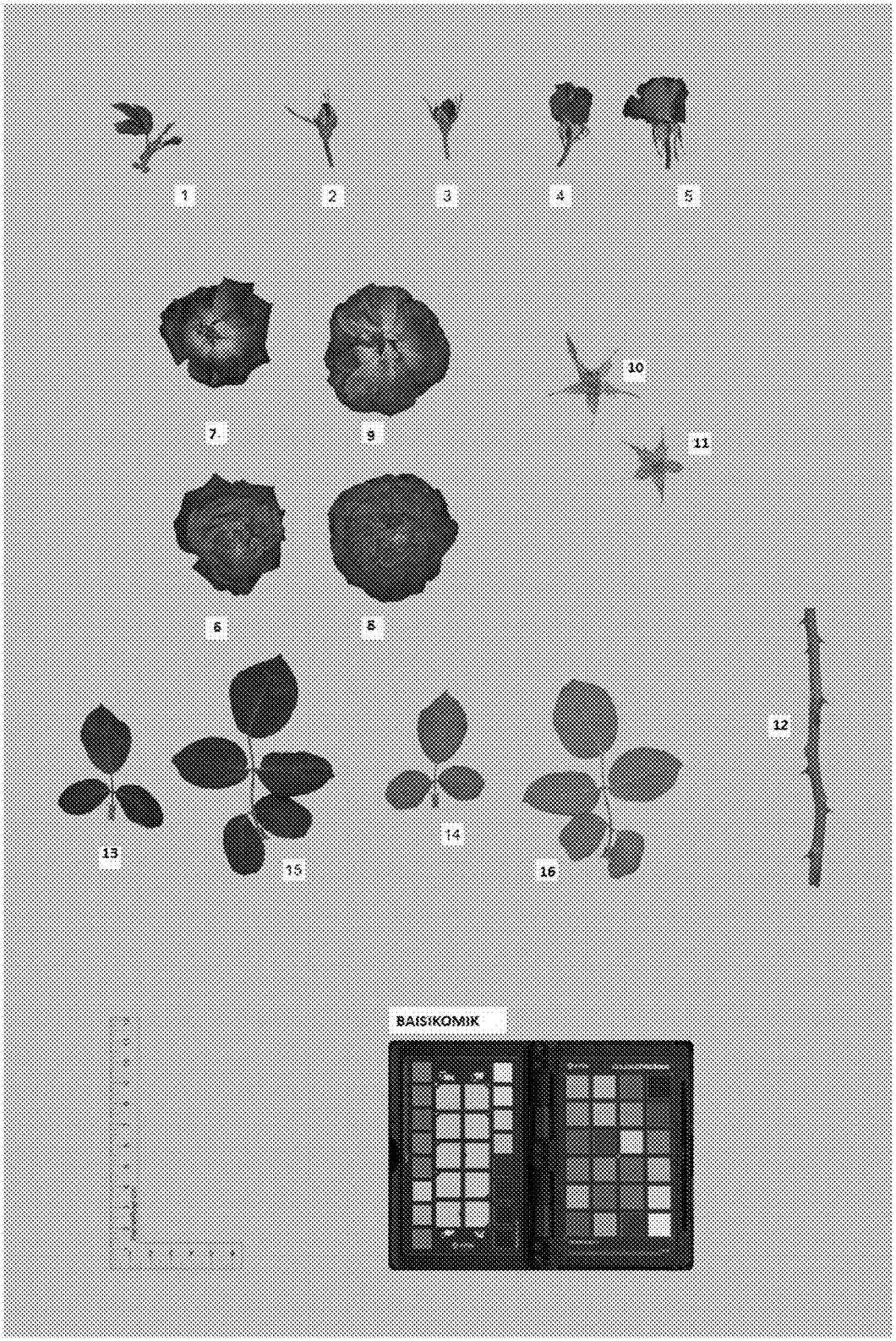
1
2
3
4
5
7
9
10
11
6
8
12
13
15
14
16
BAISIKOMIK